(12) United States Patent
Hocken et al.

(10) Patent No.: US 8,823,400 B2
(45) Date of Patent: *Sep. 2, 2014

(54) METHOD AND SYSTEM FOR CONTAMINATION SIGNATURE DETECTION DIAGNOSTICS OF A PARTICULATE MATTER SENSOR

(75) Inventors: Lary R. Hocken, Davison, MI (US); Charles S. Nelson, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 564 days.

This patent is subject to a terminal disclaimer.

(21) Appl. No.: 13/171,540

(22) Filed: Jun. 29, 2011

(65) Prior Publication Data

US 2013/0002271 A1  Jan. 3, 2013

(51) Int. Cl.
| | |
|---|---|
| G01R 27/08 | (2006.01) |
| F02D 41/14 | (2006.01) |
| F02D 41/22 | (2006.01) |
| G01N 15/06 | (2006.01) |
| G01N 27/04 | (2006.01) |

(52) U.S. Cl.
CPC .......... *F02D 41/222* (2013.01); *F02D 41/1466* (2013.01); *Y02T 10/40* (2013.01); *G01N 27/041* (2013.01); *F02D 41/1494* (2013.01); *G01N 15/0656* (2013.01)
USPC ........... 324/691; 324/693; 324/703; 324/720; 324/721; 324/705; 702/116; 702/182; 702/183; 702/189; 73/1.06; 73/1.01; 73/1.02; 73/114.01; 73/114.69; 701/30.9; 701/31.1; 701/29.7; 701/30.5; 701/31.2

(58) Field of Classification Search
CPC . G01N 27/14; G01N 27/419; G01N 33/0036; G01N 15/0656; G06F 11/30; G06F 19/00
USPC .......... 324/693, 703, 720, 601, 721; 73/1.06, 73/1.01, 1.02, 114.01, 114.69, 114.71; 701/30.9, 31.1, 29.7, 30.5, 31.2; 702/116, 182, 183, 189
See application file for complete search history.

(56) References Cited

U.S. PATENT DOCUMENTS

| | | | |
|---|---|---|---|
| 4,656,832 A | 4/1987 | Yukihisa et al. | |
| 6,634,210 B1 | 10/2003 | Bosch | |
| 8,249,827 B2 * | 8/2012 | Nelson et al. | ................. 702/183 |
| 2008/0282769 A1 | 11/2008 | Nelson | |
| 2008/0283398 A1 | 11/2008 | Nelson et al. | |
| 2009/0139081 A1 | 6/2009 | Nelson | |
| 2010/0312488 A1 * | 12/2010 | Diehl et al. | ..................... 702/23 |
| 2011/0109331 A1 | 5/2011 | Nelson et al. | |

* cited by examiner

*Primary Examiner* — Arleen M Vazquez
*Assistant Examiner* — Son Le
(74) *Attorney, Agent, or Firm* — Mark H. Svoboda

(57) ABSTRACT

A diagnostic method and system is described for diagnosing an operating condition of a conductive particulate matter sensor. The sensor has a substrate with electrical resistance that varies with temperature and two electrodes on the substrate adapted to collect particulate matter between the electrodes, thereby establishing an electrically conductive path through collected particulate matter between the electrodes that can be detected by measuring electrical resistance between the electrodes, $R_{elect}$. The diagnosis is performed by heating the substrate in the area between the electrodes and using the resistance between the electrodes to determine detecting whether contamination is present on the surface of the sensor. Heat may be maintained on the sensor to attempt to burn off a detected contaminant, and a subsequent resistance reading may be used to determine if the contaminant was successfully burned off.

6 Claims, 5 Drawing Sheets

METHOD AND SYSTEM FOR CONTAMINATION SIGNATURE DETECTION DIAGNOSTICS OF A PARTICULATE MATTER SENSOR

BACKGROUND OF THE INVENTION

This invention relates generally to sensors for detecting electrically conductive particulate matter, such as soot, and more particularly to a method and system for diagnosing potential failure modes in such sensors.

Incomplete combustion of certain heavy hydrocarbon compounds, such as heavy oils, diesel fuel, and the like may lead to particulate formation (e.g., soot). In the operation of internal combustion engines, excessive particulate formation can lead to "smoking" of the engine, which causes air pollution even though the carbon monoxide, hydrocarbons, and other pollutant components of the gaseous state exhaust emissions may be relatively low. Emission regulations require many engines to limit the levels of particulate emissions, and various control technologies such as diesel particulate filters (DPF) have been employed for this purpose.

In order to monitor the emission of particulate matter in the exhaust streams of certain types of internal combustion engines, e.g., to assess the effectiveness of DPF's, it is known to provide a particulate sensor system for detecting the level of particulate concentration emitted from an exhaust gas. Various particulate sensors have been proposed, including those shown in U.S. Pat. No. 4,656,832 issued to Yukihisa et al., U.S. Pat. No. 6,634,210 issued to Bosch et al., U.S. Pat. Publ. No. 2008/0283398 A1, U.S. Pat. Publ. No. 2008/0282769 A1, and U.S. Pat. Publ. No. 2009/0139081 A1, the disclosures of each of which are hereby incorporated by reference in their entirety.

Particulate sensors such as those described above generally have a pair of spaced apart sensing electrodes disposed on a substrate. The sensing electrodes are coupled to a measurement circuit by way of electrically conductive leads. The operating principle of the particulate sensor is based on the conductivity of the particulates (e.g., soot) deposited on (or over) the sensing electrodes. The electrical resistance between the sensing electrodes is relatively high when the sensor is clean but such resistance decreases as soot particulates accumulate. These sensors also have a heater that can be selectively activated to burn off the soot particulates to "reset" the sensor to a known, base "clean" state.

However, for diagnostic purposes, it can be difficult to distinguish between various states that may occur during various engine operating conditions, such as between: (i) a faulty state such as when the sensor is "poisoned" by a non-conductive or semi-conductive contaminant deposited on the electrodes preventing soot from contacting the electrodes, which presents as a very high resistance between the sensing electrodes, and (ii) a normal state, such as when a sensor has just been cleaned, which also presents as a very high resistance.

Accordingly, there is a need for particulate sensor diagnostics that can accurately distinguish between sensor states during various engine operating conditions.

SUMMARY OF THE INVENTION

The present invention relates to a method of diagnosing an operating condition of an electrically conductive particulate matter sensor where the sensor comprises a substrate having an electrical resistance that varies with temperature and two electrodes on the substrate adapted to collect particulate matter between the electrodes, thereby establishing an electrically conductive path through collected particulate matter between the electrodes that can be detected by measuring electrical resistance between the electrodes, $R_{elect}$. The method according to the invention comprises the steps of:

(a) commanding the provision of heat to the sensor in an amount sufficient to modify the electrical resistance of the substrate, and detecting whether $R_{elect}$ changes in a manner consistent with heating of a contaminant on the substrate;

(b) if $R_{elect}$ changes in a manner consistent with heating of a contaminant on the substrate in step (a), then diagnosing a contamination condition for the sensor.

Exemplary embodiments of the invention also relate to a storage medium encoded with machine readable computer program code for diagnosing a failure condition of an electrically conductive particulate matter sensor as described above where the storage medium includes instructions for causing a computer to implement the above-described method.

Another exemplary embodiment of the invention relates to a diagnostic system for an electrically conductive particulate matter sensor as described above, the system comprising a microprocessor in communication with the sensor and a storage medium including instructions for causing the microprocessor to implement the above-described method.

These and other advantages and features will become more apparent from the following description taken in conjunction with the drawings.

BRIEF DESCRIPTION OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

Figure 1:
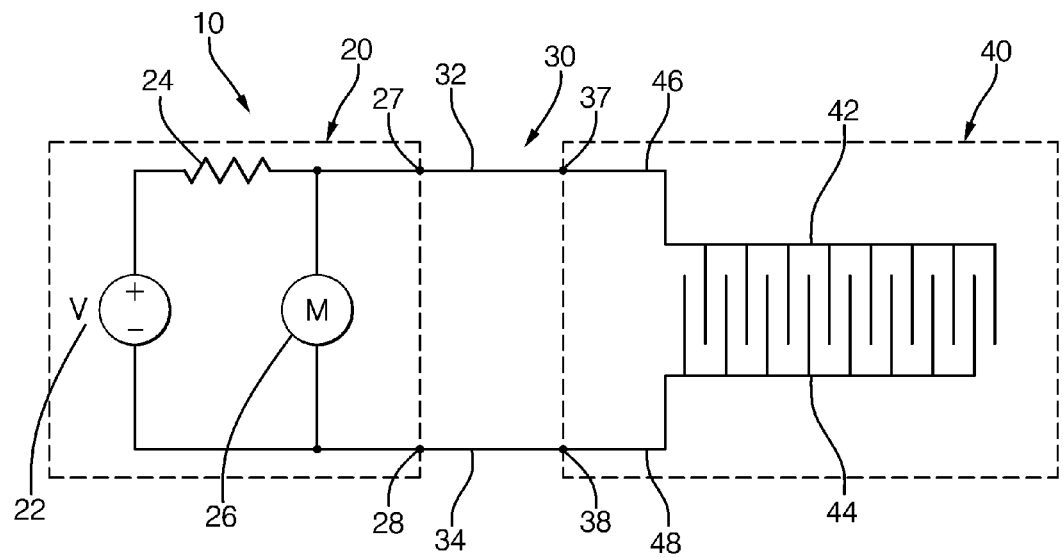
FIG. 1 is an electrical schematic of a particulate matter sensing system for which the diagnostics of the invention may be practiced.

Referring now to the Figures, where the invention will be described with reference to specific embodiments, without limiting same.

In describing and claiming algorithms according to the invention, letters and naming conventions are arbitrarily employed to represent numerical values (e.g., $R_{OBD\_hot}$ $K_{R\_OBD\_cont\_pct}$). These naming conventions are used solely to enhance the readability of the description of the invention, and are not intended to have any functional significance whatsoever. The representation of these numerical values is intended to be precisely the same as if, for example completely arbitrary descriptions (e.g., $R_1$, $R_2$, $K_1$, $K_2$) had been used. Additionally, it should be noted that in the practice of the invention, measurements of resistance between the electrodes may be made by applying a known current across the electrodes, measuring the voltage differential between the electrodes and calculating the resistance using Ohm's law, as is well-known in the art. It would of course be possible to simply use the voltage values in place of resistance values in the algorithm of the invention by converting the various resistance constants and equations to voltage, and such alternative embodiments are considered to be within the scope of the invention.

In general, an exemplary particulate matter sensor that can be used in the practice of the present invention comprises a sensing element and a heating element, wherein the sensing element may comprise, but is not limited to, at least two sensing electrodes in proximity to each other on a substrate and configured so as to accumulate particulate matter therebetween, and wherein the heating element may comprise, but is not limited to, a temperature sensor, and a heater. The sensor may include a multi-layered structure comprising the sensing element, the temperature sensor, the heater, and a combination comprising at least one of the foregoing, contained in a single structure formed, e.g., by multi-layer technology.

The sensing electrodes can include metals, such as, gold, platinum, osmium, rhodium, iridium, ruthenium, aluminum, titanium, zirconium, and the like, as well as, oxides, cermets, alloys, and combinations comprising at least one of the foregoing metals. In an exemplary embodiment, the sensing electrode can comprise a platinum/alumina cermet wherein the platinum is about 70 wt % (weight percent) to about 98 wt % of the sensing electrode. In another exemplary embodiment, the sensing electrode comprises about 93 wt % to about 95 wt % platinum, where weight percent is based on the total dry weight of the cermet. Each sensing electrode may be composed of the same or different material as the other sensing electrode(s).

The sensing electrodes can be formulated in any fashion. In one exemplary embodiment, however, the sensing electrodes are formed by first preparing an ink paste by mixing an electrode forming-metal powder (e.g., platinum, gold, osmium, rhodium, iridium, ruthenium, aluminum, titanium, zirconium, and the like, or combinations of at least one of the foregoing) with oxides in a sufficient amount of solvent to attain a viscosity suitable for printing. The oxides used to form the sensing electrodes may include those oxides that do not promote the oxidation of particulates and that do not lower the burn-off temperature of the particulates. Non-suitable oxides are, e.g., copper oxide, cerium oxide, and iron oxide. The ink paste forming the sensing electrode can then be applied to an electrode substrate via sputtering, chemical vapor deposition, screen printing, flame spraying, lamination, stenciling, or the like.

The sensing electrodes may be disposed onto the electrode substrate such that a constant distance of separation between each sensing electrode is created. The width of the distance separating the sensing electrodes can vary widely, depending upon desired design parameters. In one exemplary embodiment, this distance comprises a width of separation of about 0.01 to about 0.12 millimeter (mm).

Both the heater and the temperature sensor, forming in whole or in part, the heating element, can comprise various materials. Possible materials include platinum, gold, palladium, and the like; and alloys, oxides, and combinations comprising at least one of the foregoing materials, with platinum/alumina, platinum/palladium, platinum, and palladium. The heater and temperature sensor can be applied to the sensor in any fashion, such as by sputtering, chemical vapor deposition, screen printing, flame spraying, lamination, and stenciling among others. In one embodiment, the heater can comprise a thickness of about 3 to about 50 micrometers. In another embodiment the heater thickness is about 5 to about 30 micrometers. In yet another embodiment, the heater thickness is about 10 to about 20 micrometers.

The sensor may further comprise various substrates useful in electrically isolating and protecting the sensing element and the heating element from the temperature surrounding the sensor and/or from the thermal reduction of the condensed particulates during the self-regeneration cycles. The substrates include, but are not limited to, an electrode protective layer, an electrode substrate, an isolation layer, an insulating temperature substrate, a heater substrate, insulating substrates, wherein the number of insulating substrates is sufficient to prevent disruptive ionic or electrical communication between the heating element and the sensing electrode (e.g., about 2 to about 3 insulating substrates), and combinations comprising at least one of the foregoing.

The substrates can comprise non-ionically conducting, electrically insulating materials. Possible electrically insulating materials include oxides, such as alumina, zirconia, yttria, lanthanum oxide, silica, and combinations comprising at least one of the foregoing, or any like material capable of inhibiting electrical communication and providing physical protection. In order to hinder electrical communication between the components of the sensor, the substrates may be composed of a high purity oxide; e.g., less than about 10.0 wt % impurities. In another embodiment, the substrates comprise less than about 8.0 wt % impurities. In yet another embodiment, the substrates comprise less than about 5.0 wt % impurities, wherein the weight percent of the impurities is based on the total weight of the substrate. Although the composition of the individual substrates can vary, in certain embodiments they comprise a material having substantially similar coefficients of thermal expansion, shrinkage characteristics, and chemical compatibility in order to minimize, if not eliminate, delamination and other processing problems. Alkaline (e.g., sodium, potassium, lithium, and the like) oxides should be avoided as they can be easily reduced to form impurities in the heater, temperature sensor, and the sensing electrodes.

In general, each of the substrates can be of sufficient size to support the entire length of the sensing electrodes, the temperature sensor, and/or the heater. The thickness of each substrate can be determined based on the desired thermal response time of the self-regeneration cycle, where shorter thermal response times require a smaller thickness. The thickness of each substrate can be up to about 200 micrometers thick. In an exemplary embodiment, the substrate thickness is about 50 to about 180 micrometers. In another exemplary embodiment, the substrate thickness is about 140 to about 160 micrometers. The substrates can be formed using ceramic tape casting methods, and the like.

The sensor may further comprise various leads responsible for electrically communicating the sensor with the sensor circuit. One end of each sensing electrode, one end of the temperature sensor, and one end of the heater may have a connecting point to which one end of at least one lead may be attached. Each sensing electrode may be electrically connected with at least one lead extending from one end of each sensing electrode; and the heater is electrically connected with at least one lead extending from one end of the heater.

After acquiring the components of the sensor, the sensor may be constructed according to thick film multilayer technology such that the thickness of the sensor allows for good thermal response time toward the thermal cycle of sensor regeneration. In an exemplary embodiment, the sensor element thickness is about 0.1 to about 3.0 millimeter (mm).

FIG. 1 is an electrical schematic of a particulate matter sensing system 10. The system may be generally considered as partitioned as indicated into a controller portion 20, a wiring harness portion 30, and a sensing element portion 40. The controller portion 20 comprises a means for measuring the impedance of a circuit connected thereto. In the exemplary controller portion 20 in FIG. 1, the impedance measurement means includes a voltage source 22 that provides a voltage value $V_{supply}$, a pull-up resistor 24 having a resistance value $R_{pullup}$, and a voltage measurement means 26. While voltage source 22 is depicted in FIG. 1 as a DC source with a given polarity, it will be appreciated that voltage source 22 can alternatively be an AC source, a DC source having opposite polarity from what is depicted, or a source providing both an AC and a DC voltage component, without departing from the inventive concept described herein. The controller portion 20 electrically interfaces to the wiring harness portion 30 by connection means 27 and 28. The wiring harness portion 30 includes conductors 32 and 34. The wiring harness portion 30 electrically interfaces to the sensing element portion 40 by connection means 37 and 38. The sensing element portion 40 includes a first electrode 42 electrically connected by conductor 46 to connection means 37, and a second electrode 44 electrically connected by conductor 48 to connection means 38.

As formed on the sensing element, the first electrode 42 is electrically isolated from the second electrode 44, so that a sensing element 40 in the absence of particulate matter appears electrically as an open circuit when measured between connection means 37 and connection means 38. In the absence of particulate matter, the voltage measured by measurement means 26 will be essentially equal to $V_{supply}$, the voltage provided by voltage source 22.

The first electrode 42 and second electrode 44 may be shaped in the form of interdigitized fingers with a small gap therebetween. In operation, particulate matter that is deposited on the sensing element so as to bridge the gap between the electrodes 42, 44 can be detected because the particulate matter forms a conductive path bridging the normally open circuit between the electrodes 42, 44. If the resistance of the particulate matter bridging the electrodes is assigned the value $R_{particulate}$, the voltage measured by measurement means 26 will be:

$$V_{measured} = V_{supply} \frac{R_{particulate}}{R_{pullup} + R_{particulate}}$$

As particulate matter accumulates between first electrode 42 and second electrode 44, the resistance $R_{particulate}$ will decrease, and the voltage $V_{measured}$ at measurement means 26 will decrease from the maximum value of $V_{supply}$. The controller portion can thereby determine the impedance connected across connection means 27 and 28 as a function of the voltage measured between points 27 and 28.

Figure 2:
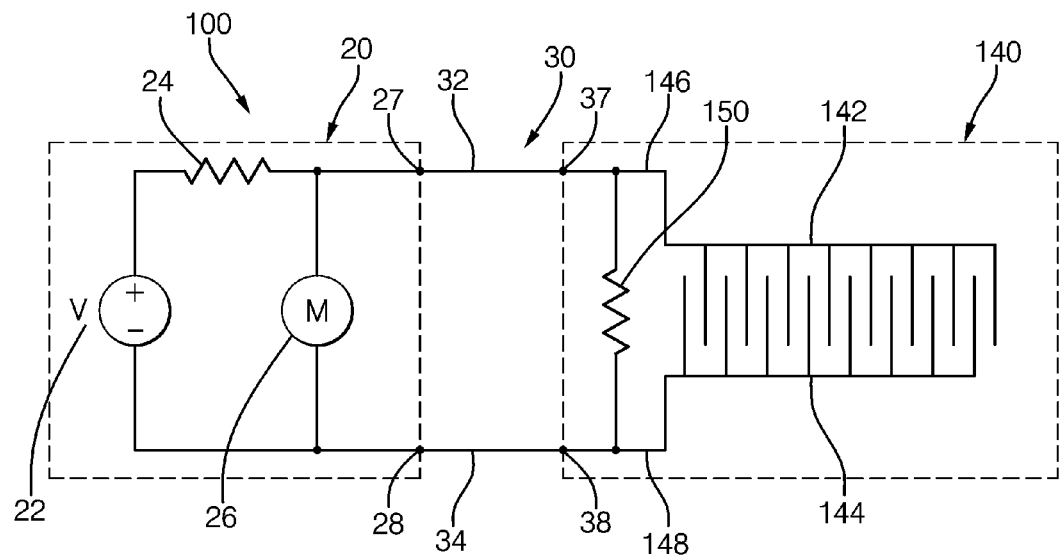
FIG. 2 is an electrical schematic of an alternative particulate matter sensing system incorporating a bias resistor for which the diagnostics of the invention may be practiced.

FIG. 2 is an electrical schematic of an alternative particulate matter sensing system 100 incorporating a bias resistor, as disclosed in U.S. patent application Ser. No. 12/947,867 filed Nov. 17, 2010 titled "SELF DIAGNOSTICS OF A PARTICULATE MATTER SENSOR", the contents of which are incorporated by reference in their entirety. Controller portion 20 and wiring harness portion 30 are essentially the same as in the system 10 in FIG. 1. The sensing element portion 140 includes a first electrode 142 electrically connected by conductor 146 to connection means 37, and a second electrode 144 electrically connected by conductor 148 to connection means 38. The sensing element portion 140 in FIG. 2 contains an additional bias resistor 150 having a resistance value of $R_{bias}$ electrically connected between conductors 146 and 148. The resistance of the sensing element $R_{sensor}$ as measured between connection means 37 and connection means 38 is the parallel combination of $R_{bias}$ and the resistance resulting from particulate matter bridging the gap between the first electrode 142 and the second electrode 144. $R_{sensor}$ can be represented mathematically as:

$$R_{sensor} = \frac{R_{bias} \times R_{particulate}}{R_{bias} + R_{particulate}}$$

In the absence of particulate matter on sensing element 140, the term $R_{particulate}$ is very large compared to $R_{bias}$, and the effective sensor resistance $R_{sensor}$ is essentially equal to $R_{bias}$. This condition provides the maximum resistance value of $R_{sensor}$. As particulate matter accumulates so as to bridge the gap between the first electrode 142 and the second electrode 144, the effective sensor resistance $R_{sensor}$ will decrease from its maximum value of $R_{bias}$.

For the particulate matter sensing system 100 depicted in FIG. 2, the voltage measured by measurement means 26 will be:

$$V_{measured} = V_{supply} \frac{R_{sensor}}{R_{pullup} + R_{sensor}}$$

In the absence of particulate matter, the value of $R_{sensor}$ will be at its maximum and will essentially equal $R_{bias}$. Under this condition, the voltage measured by measurement means 26 will be:

$$V_{measured} = V_{supply} \frac{R_{bias}}{R_{pullup} + R_{bias}}$$

Figure 3:
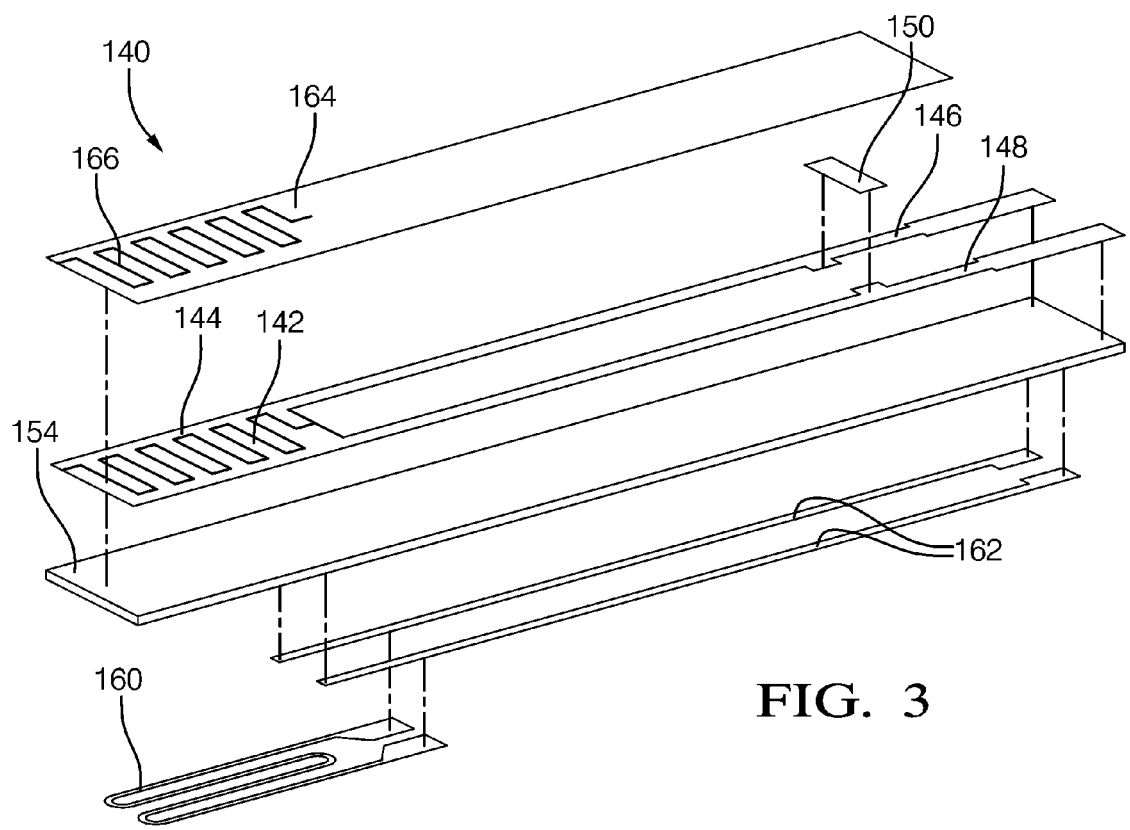
FIG. 3 is an exploded perspective view of a sensing element as found in the particulate matter sensing system of FIG. 2.

FIG. 3 is an exploded perspective view of the sensing element 140 of FIG. 2. The sensing element 140 includes an electrically insulating substrate 154. While shown as a single layer, it will be appreciated that substrate 154 may be formed by laminating together a plurality of layers. Conductive material disposed on one surface of substrate 154 is patterned to form conductors 146 and 148 and electrodes 142 and 144. Resistor material to form bias resistor 150 is deposited so as to form a resistive path between conductors 146 and 148. A protective layer 164 may also be included to protect the conductive material that forms electrodes 142 and 144, as well as portions of the conductors 146, 148 that may be exposed to abrasive particles in the gas stream being measured. The protective layer 164 includes an open area 166 exposing the gap between the electrodes 142 and 144 to allow particulate matter to bridge the electrodes 142 and 144. The protective layer 164 may also extend to cover bias resistor 150.

A particulate matter sensor may also include a heating means that is controllable to raise the temperature in the vicinity of the electrodes 142, 144 on the sensing element. Raising the temperature sufficiently will result in the particulate matter being removed from the surface of the sensing element, thereby restoring the resistance of the area between the sensing electrodes 142, 144 to a high resistance or essentially open circuit condition. This open circuit condition appears electrically in parallel with the bias resistor 150, so that the total resistance measured between connection means 37 and connection means 38 is restored to $R_{bias}$. The sensing element 140 depicted in FIG. 4 includes a heater 160 and heater leads 162, on the opposite surface of the substrate from the electrodes 142, 144. The heater 160 is positioned to allow the heater 160 to clean the particulate matter from the vicinity of the electrodes 142, 144 when the heater 160 is electrically powered by supplying current through heater leads 162.

Figure 4:
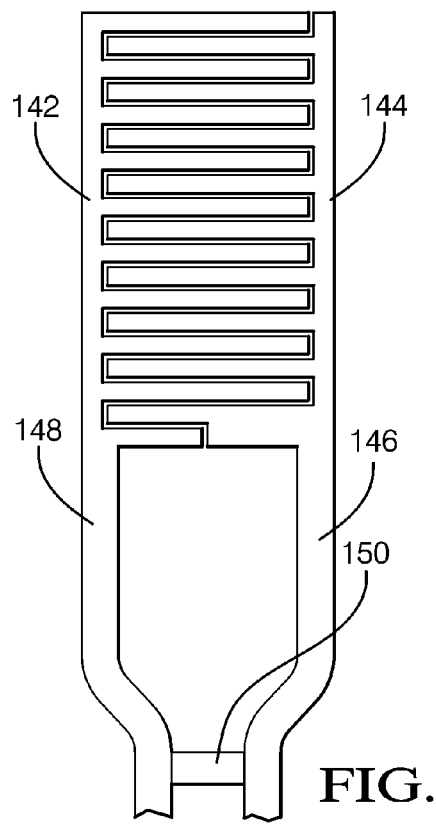
FIG. 4 is a plan view of a sensing element as found in the particulate matter sensing system of FIG. 2.

FIG. 4 is a plan view of the conductor and resistor pattern of a sensing element 140 as depicted in FIGS. 2 and 3. Bias resistor 150 is located remote from the first electrode 142 and the second electrode 144 to minimize heating of the bias resistor 150 when the heater (not shown) is activated to clean the particulate matter from the vicinity of the electrodes 142, 144.

The foregoing discussion assumes that the substrate 154 on which the electrodes are deposited has infinite resistivity. In fact, candidate substrate materials have a high but measurable resistivity that further depends on temperature. For example, the CRC Materials Science and Engineering Handbook, Third Edition (CRC Press, 2001) provides on page 959 the resistivity data for alumina (aluminum oxide, $Al_2O_3$) shown in Table 1 below. The effect of temperature sensitivity of the resistivity of the substrate material is disclosed in U.S. patent application Ser. No. 12/614,654, the contents of which are hereby incorporated by reference.

TABLE 1

Resistivity of Aluminum Oxide ($Al_2O_3$), from the CRC
Materials Science and Engineering Handbook, Third Edition, page 959

| Resistivity (Ω-cm) | Temperature Range of Validity |
|---|---|
| >10 × 10$^{14}$ | 25° C. |
| 2 × 10$^{13}$ | 100° C. |
| 1 × 10$^{13}$ | 300° C. |
| 6.3 × 10$^{10}$ | 500° C. |
| 5.0 × 10$^{8}$ | 700° C. |
| 2 × 10$^{6}$ | 1000° C. |

Figure 5:
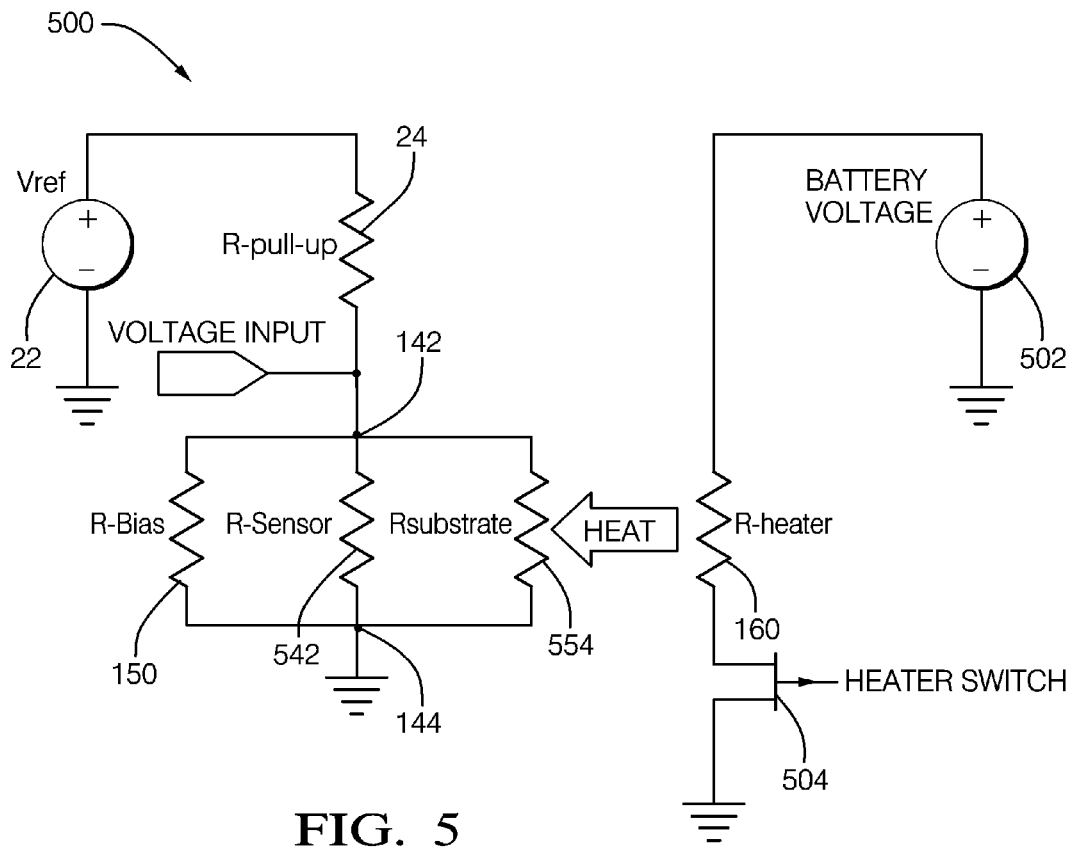
FIG. 5 is an electrical schematic that includes aspects of the present invention.

Referring now to FIG. 5, a non-limiting example of a particulate sensor system 500 is illustrated. The system includes a reference voltage source 22, a pull-up resistor 24, a bias resistor 150, and an arrangement for measuring the resistance 542 of material deposited between the sensing electrodes 142 and 144, as previously disclosed in relation to FIG. 2. FIG. 5 also includes a resistance 554, in parallel with resistances 150 and 542, where resistance 554 represents the resistance resulting from the resistivity of the material that forms the substrate (154 in FIG. 3) in contact with electrodes 142 and 144. It will be appreciated that in an actual sensor there will also be resistance between the heater 160 and the electrodes 142 and 144 due to the resistivity of the material that forms the substrate (154 in FIG. 3). The effect of the resistance between the heater 160 and the electrodes 142, 144 is negligible because the thickness of substrate 154 is so much larger than the distance between electrodes 142 and 144. FIG. 5 also includes a voltage source 502 configured to deliver energy to heater 160 when heater switch 504 is turned on.

When heater 160 is energized heat is coupled to resistances 542 and 554, causing the temperatures of these resistances to increase. Bias resistor 150 is located at the end of sensing element 140 remote from heater 160, so bias resistor 150 will experience less heating than resistances 542 and 544. The materials that form resistive elements 542 and 554 each have a distinct temperature coefficient of resistance (TCR), such that the behavior of the sensor with the heater energized can be used to diagnose various conditions of the sensor.

Figure 6:
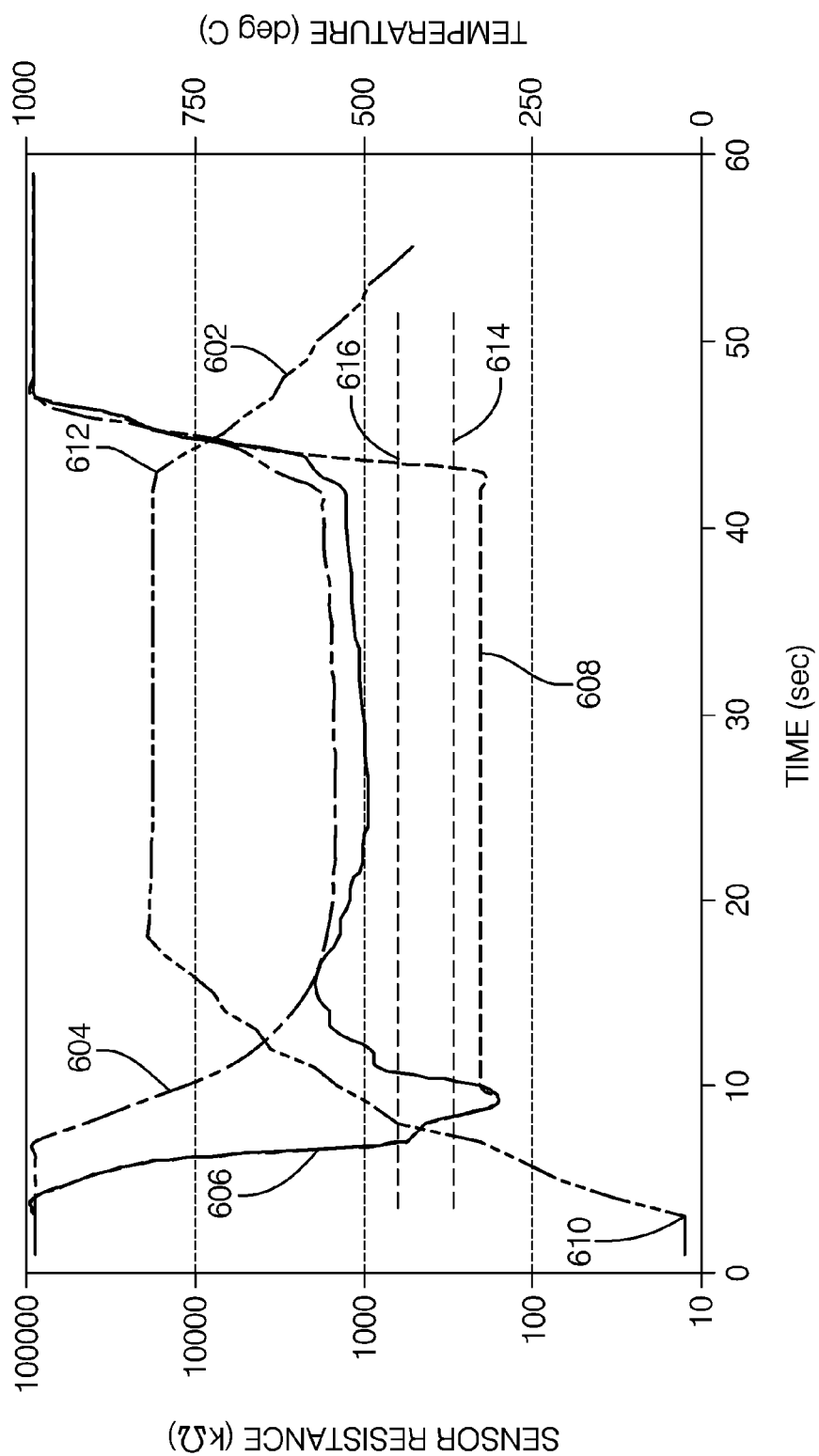
FIG. 6 is a chart illustrating values of parameters that may be observed in a particulate matter sensing system that incorporates aspects of the present invention.

FIG. 6 is a graph that illustrates a non-limiting example of parameters that may be observed in a particulate sensor system under various conditions. In FIG. 6, trace 602 represents substrate temperature, plotted against the y-axis scale on the right side of the graph. In FIG. 6, when the heater is energized at the time indicated by point 610, the temperature represented by trace 602 rises until it reaches an equilibrium value. At time 612, the heater is turned off, resulting in the substrate temperature decreasing.

The other traces in FIG. 6 represent resistances that may be measured across the sensor, plotted against the logarithmic scale shown on the y-axis on the left side of the graph. Resistance values higher than 100,000 kΩ are treated as if clamped to a maximum value of 100,000 kΩ because in the exemplary embodiment it is not necessary to know the exact value of resistances greater than 100,000 kΩ. In FIG. 6, trace 604 represents the behavior of a normal particulate sensor. The resistance represented by trace 604 starts at a high value, indicating no particulate matter deposited between the sensing electrodes (e.g. electrodes 142 and 144 in FIGS. 2 through 4). As the substrate temperature increases due to the influence of the heater after the heater is turned on at point 610, the resistance measured between the electrodes changes as a result of the TCR of the substrate material as illustrated in Table 1 above. This change in substrate resistance depends on factors such as the substrate material and the geometry of elements of the sensor, but for a given sensor a normal heater signature can be predetermined.

As shown by trace 604, a high resistance reading before the heater is energized may indicate a normal sensor condition. However, it is possible that a contaminant that is not electrically conductive at normal exhaust temperatures (e.g. 150° C. to 450° C.) may be deposited on the surface of the sensor. Such a contaminant may comprise material from additives in fuel or lubricating oil that enter the gas stream to which the sensor is exposed. The presence of such a contaminant on the surface of the particulate matter sensor may insulate the sensing electrodes from receiving the conductive particulate matter that the sensor is intended to detect, thus preventing the sensor from recognizing soot in an exhaust stream.

Certain types of contaminants are electrically non-conductive at low temperatures and become conductive at higher temperatures. The behavior of a sensor contaminated with this type of contaminant is shown in trace 606 in FIG. 6. Because the resistance of the contaminant appears electrically in parallel with the resistance due to the substrate, when the heater is energized at point 610 and the contaminant resistance decreases the total resistance measured across the electrodes as shown in trace 606 decreases more rapidly than the normal heater signature shown in trace 604. Additionally, the lowest resistance level in trace 606 that is achieved with the heater energized is lower than the lowest resistance level reached in the normal heater signature 604. Either the time response of the resistance decrease, the magnitude of the resistance decrease, or a combination of response time and magnitude may be used to distinguish a contaminated sensor from a normal sensor. For example a resistance level indicated as level 614 in FIG. 6 may represent a detection threshold, such that a sensor resistance with the heater actuated that falls below the threshold 614 is diagnosed as a contaminated sensor. The resistance value corresponding to threshold 614 may depend on the actual temperature of the sensor element. The hotter the element is, the more conductive the contamination and soot become, and a lower threshold 614 may be needed to recognize a contaminated sensor.

A contaminant present on the sensing element may burn off as the temperature of the sensor is elevated, depending on the oxidation temperature of the contaminant. This behavior is also shown in trace 606, where after the initial minimum the detected resistance increases due to the removal of the contaminant as a result of the continued application of heat. Burn-off of the contaminant is evidenced by trace 606 approaching the behavior of normal heater signature trace 604.

Alternatively, a contaminant material may be of such a nature that it does not burn off at the substrate temperatures achieved as a result of the heater energy. Such a contaminant would have a resistance signature as indicated by trace 608, where the resistance remains low until the heater is turned off at time 612. To detect a contaminant that does not burn off, the resistance of the sensor may be compared to a second detection threshold, such as level 616 in FIG. 6. If the sensor resistance falls below the first detection threshold 614 and never rises above the second detection threshold 616 while the heater is energized, the sensor may be diagnosed as having a contaminant particle or contaminant coating that did not burn off. This contaminant may be burned off by regeneration at a higher temperature and/or for a longer duration.

Figure 7:
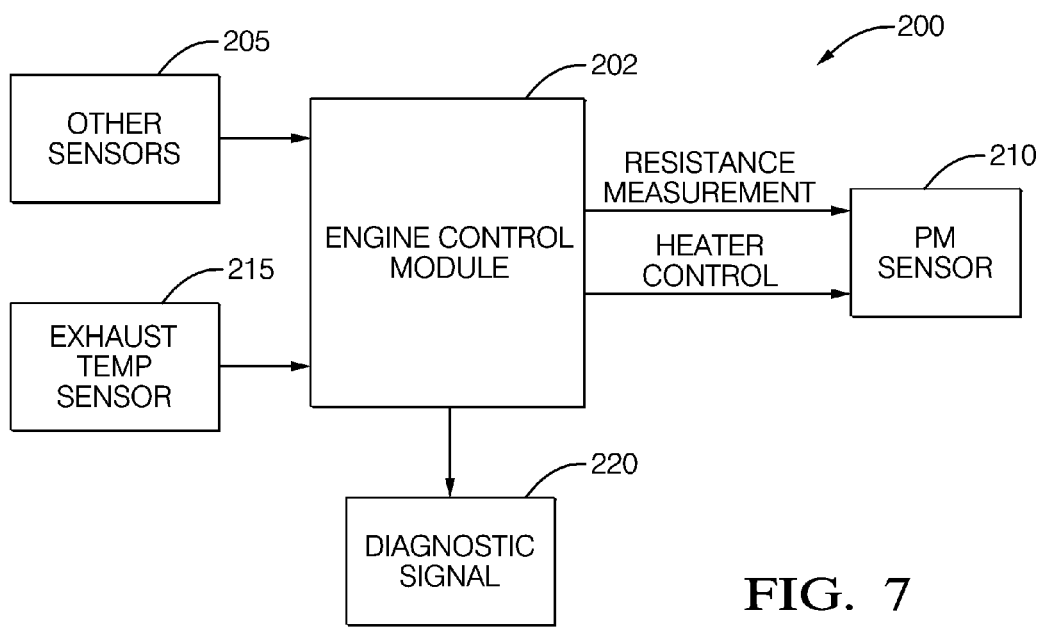
FIG. 7 is a schematic illustration of an engine control module and a particulate matter sensor.

The method and system of the invention may be used in conjunction with a sensor for conductive particulate matter of any sort and in a variety of environments. In one exemplary embodiment, the sensor is a soot sensor in the exhaust stream of an internal combustion engine such as a diesel engine. Referring now to FIG. 7, a non-limiting example of a particulate sensor diagnostic system 200 is illustrated, which includes a particulate matter sensor 210. The diagnostic system comprises a controller or an engine control module (ECM) 202. Alternatively to an ECM, a stand-alone diagnostic or combined sensor and diagnostic control module may be used, provided that it is able to communicate with an ECM in order to obtain information from the ECM, such as exhaust temperature, engine operating state, etc. ECM 202 comprises among other elements a microprocessor for receiving signals indicative of the vehicle performance as well as providing signals for control of various system components, read only memory in the form of an electronic storage medium for executable programs or algorithms and calibration values or constants, random access memory and data buses for allowing the necessary communications (e.g., input, output and within the ECM) with the ECM in accordance with known technologies.

In accordance with an exemplary embodiment the controller will comprise a microcontroller, microprocessor, or other equivalent processing device capable of executing commands of computer readable data or program for executing a control algorithm. In order to perform the prescribed functions and desired processing, as well as the computations therefore (e.g., the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. As described above, exemplary embodiments of the present invention can be implemented through computer-implemented processes and apparatuses for practicing those processes.

The ECM receives various signals from various sensors in order to determine the state of the engine as well as vary the operational state and perform diagnostics for example, the ECM can determine, based on its input from other sensors 205 and logic and control algorithms whether the engine is being started in a "cold start" state as well as perform and/or control other vehicle operations. Some of the sensors that may be included in other sensors 205 which provide input to the ECM 202 include but are not limited to the following: engine coolant temperature sensor, engine speed sensor, exhaust oxygen sensor, engine temperature, engine mass air flow and the like. The sensors used may also be related in part to the type of engine being used (e.g., water cooled, air cooled, diesel, gas, hybrid, etc.). The ECM 202 also receives input from exhaust temperature sensor 215, which may be a temperature probe located in the exhaust stream in proximity to the particulate matter sensor or other equivalent means or method for measuring the exhaust temperature.

In accordance with operating programs, algorithms, look up tables and constants resident upon the microcomputer of the ECM various output signals, including control of heater element 160 and diagnostic signal 220 are provided by the ECM. While the control signals for heater element 160 and diagnostic signal 220 are relevant to the practice of the invention, the ECM may also provide other control signals to control the engine (e.g., limiting or shutting off fuel flow as well as closing or opening the intake and exhaust valves of the engine) as well as performing other vehicle operations including but not limited to: fuel/air flow control to maintain optimum, lean or rich stoichiometry as may be required to provide the required torque output; spark timing; engine output; and providing on board malfunctioning diagnostic (OBD) means to the vehicle operator.

Figure 8:
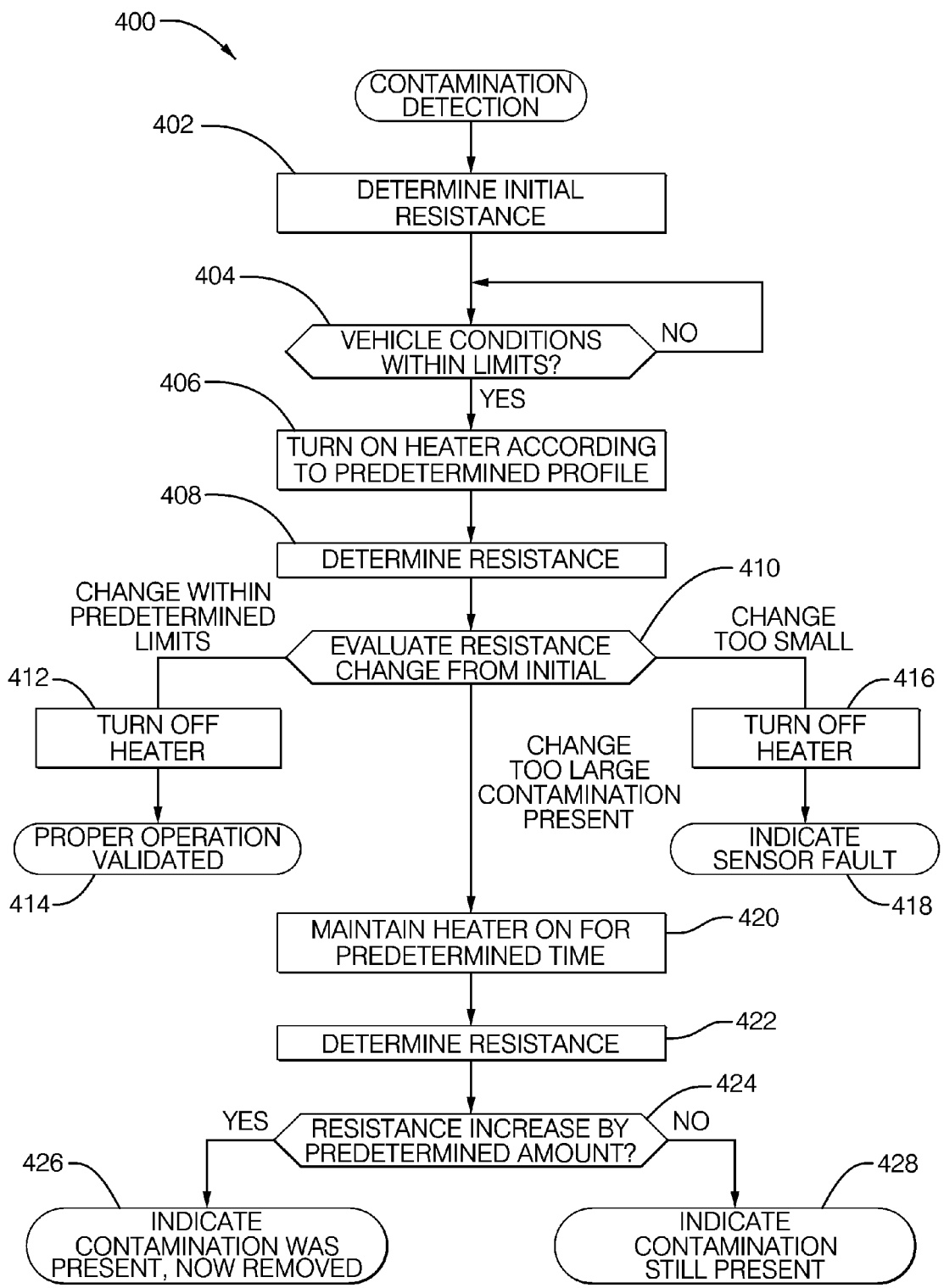
FIG. 8 constitutes a schematic illustration of a flow chart illustrating portions of a control algorithm contemplated for use in exemplary embodiments of the present invention.

Turning now to FIG. 8, a flow chart illustrating portions of a control algorithm 400 in accordance with a nonlimiting exemplary embodiment of the invention is illustrated for performing diagnostics on a particulate matter sensor based on response to heating of the sensor substrate. In this exemplary embodiment, control algorithm 400 is implemented as the result of an ECM-initiated diagnostic. The diagnostic routine measures the initial resistance between the sensor electrodes in step 402 and stores the value in the ECM as $R_{OBD\_init}$.

The algorithm logic path then moves to decision node 404 where the algorithm assesses whether conditions are within limits for a heater-based regeneration of the particulate matter to occur. The purpose of this assessment is to ensure that the conditions are satisfactory for the rigorous heating used to induce a measurable electrical conductivity change in the substrate. Such a heating profile may be similar or identical to the heating profile used to burn off accumulated particulate matter during a sensor regeneration. The criteria used to assess whether the conditions are satisfactory may include (but are not limited to): an upstream diesel particulate filter (DPF) not being in regeneration mode itself (as such a regeneration in combination with activation of the heater in the heater signature detection particulate matter sensor diagnostic may cause overheating of the sensor, and also regeneration of the DPF could cause discharge of contaminants from the DPF that could interfere with the particulate matter sensor diagnostic) and/or the air flow exhaust flow volumes not being too high for the heater to sufficiently regenerate (e.g., 75 msec) or too low so as to risk damage to the heater circuit (e.g., 5 m/sec). If the criteria in decision node 404 are not met, the algorithm holds until they are met. Once the criteria in decision node 404 have been met, the algorithm moves on to box 406 to continue the diagnostic algorithm. It is to be noted that if at any time during the test the vehicle conditions are determined to be out-of-range, the heater is turned off and the diagnostic algorithm is restarted.

In box 406, the algorithm turns on the sensor heater and starts a timer using an internal clock of the ECM. In box 406, the heater is initially powered according to a profile where the heat generated is sufficient to evaporate any liquid water such as water vapor condensate that may happen to be present between the electrodes, but not so great as to cause cracking or other damage to the sensor substrate as could happen if high heat were applied before condensate had evaporated. Once gradual heating has been applied long enough to drive off any condensate, greater amounts of heat, sufficient to induce an electrical conductivity change in the substrate, are applied. In one exemplary embodiment where the substrate is an alumina substrate containing approximately 4% $SiO_2$ glass additive(s), the heat is sufficient to induce a temperature between about 500° C. and 800° C., as measurable reductions in the resistance of such materials are observed as temperatures approach and exceed 500° C., and 800° C. is close to the maximum temperature achievable by an exemplary heater.

After step 406, the algorithm proceeds to box 408, which begins a decision branch where the resistance between the electrodes is observed to see if it changes in a manner consistent with the heating of the sensor element. In box 408, resistance between the sensor electrodes is measured and the resulting value is saved as $R_{OBD\_hot}$, and the algorithm moves on to decision node 410.

In decision node 410, the algorithm evaluates the magnitude of the difference between the measured resistance value $R_{OBD\_hot}$ and predetermined thresholds based on $R_{OBD\_init}$. If $R_{OBD\_hot}$ is not less than a predetermined level, that is if the resistance change is less than the change that would have been expected due to the change in electrical resistivity of the sensor substrate resulting from the heat being applied by the heater, then the algorithm turns off the heater in step 416 and diagnoses a sensor fault in step 418. Such a sensor fault could occur, for example, as a result of an open circuit in the heater or in the circuitry or wiring driving the heater. Further description of this diagnostic may be found in the disclosure of U.S. patent application Ser. No. 12/614,654 published as U.S. Patent Application Publication 2011/0109331, the contents of which are hereby incorporated by reference.

If the determination in step 410 is that the measured resistance value $R_{OBD\_hot}$ indicates a change from $R_{OBD\_init}$ that is consistent with a properly operating heater, then the algorithm turns off the heater in step 412. The algorithm proceeds to step 414, where the algorithm diagnoses a validation that the sensor is in proper working order and reports the same to the ECM system diagnostic function.

If the determination in step 410 is that the measured resistance value $R_{OBD\_hot}$ indicates a change from $R_{OBD\_init}$ that is exceeds a value (e.g. threshold 614 in FIG. 6) that would be consistent with a properly operating heater, this is an indication of contamination on the sensor. In this case, the algorithm proceeds to step 420, where the heater is maintained on for a predetermined period of time sufficient to attempt burn-off of the contaminant. At the end of the time period in step 420, the resistance is again measured in step 422. The algorithm then proceeds to decision node 424, which determines if the resistance increased by a predetermined amount (e.g. threshold 616 in FIG. 6), consistent with removal of the contaminant, during the heating in step 420. If the result of decision node 424 is that the resistance did increase sufficiently, the algorithm proceeds to step 426, where the algorithm provides indication to the ECM that contamination had been present on the sensor but was effectively removed. If the result of decision node 424 is that the resistance did not increase sufficiently, the algorithm proceeds to step 428, where the algorithm provides indication to the ECM that contamination is on the sensor and was not removed by the heating process in step 420. Once the contamination determination is complete, the heater may be turned off.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

Having thus described the invention, it is claimed:

1. A method of diagnosing an operating condition of an electrically conductive particulate matter sensor, said sensor comprising a substrate having an electrical resistance that varies with temperature and two electrodes on said substrate adapted to collect particulate matter between the electrodes, thereby establishing an electrically conductive path through collected particulate matter between the electrodes that can be detected by measuring electrical resistance between the electrodes, $R_{elect}$, said method comprising the steps of:
   (a) commanding the provision of heat to the sensor in an amount sufficient to modify the electrical resistance of the substrate, and detecting whether $R_{elect}$ changes in a manner consistent with heating of a contaminant on the substrate;
   (b) if $R_{elect}$ changes in a manner consistent with heating of a contaminant on the substrate in step (a), then diagnosing a contamination condition for the sensor;
   wherein said sensor includes a heater element adapted to heat an area between said electrodes, and step (a) comprises the steps of:
   (1) measuring $R_{elect}$ before activating the heater element and storing the value as $R_{OBD\_init}$;
   (2) activating the heater element for a first period of time; while periodically measuring $R_{elect}$, and storing the value as $R_{OBD\_Rhot}$;
   (3) comparing $R_{OBD\_Rhot}$ to a predetermined percentage $K_{R\_ROBD\_Rinit}$;
   (4) if $R_{OBD\_Rhot}$ is not less than the predetermined percentage $K_{R\_ROBD\_Rcont\_Rpct}$ of $R_{OBD\_Rinit}$, then determining that $R_{elect}$ did not change in a manner consistent with heating a contaminated substrate; and
   (5) if $R_{OBD\_Rhot}$ is less than the predetermined percentage $K_{R\_ROBD\_Rcont\_Rpct}$ of $R_{OBD\_Rinit}$ as determined in step (3) during said first period of time, then determining that $R_{elect}$ changed in a manner consistent with heating a contaminated substrate.

2. A method of diagnosing an operating condition of an electrically conductive particulate matter sensor, said sensor comprising a substrate having an electrical resistance that varies with temperature and two electrodes on said substrate adapted to collect particulate matter between the electrodes, thereby establishing an electrically conductive path through collected particulate matter between the electrodes that can be detected by measuring electrical resistance between the electrodes, $R_{elect}$, said method comprising the steps of:
   (a) commanding the provision of heat to the sensor in an amount sufficient to modify the electrical resistance of the substrate, and detecting whether $R_{elect}$ changes in a manner consistent with heating of a contaminant on the substrate;

(b) if $R_{elect}$ changes in a manner consistent with heating of a contaminant on the substrate in step (a), then diagnosing a contamination condition for the sensor;

(c) if $R_{elect}$ changes in a manner consistent with heating of a contaminant on the substrate in step (a), then (i) maintaining the provision of heat for a predetermined time, (ii) determining after the lapse of the predetermined time whether $R_{elect}$ changes in a manner consistent with the contaminant being removed from the sensor, then (iii) if $R_{elect}$ changes in a manner consistent with the contaminant being removed from the sensor diagnosing that the contaminant was removed from the sensor, or if $R_{elect}$ does not change in a manner consistent with the contaminant being removed from the sensor diagnosing that the contaminant was not removed from the sensor.

3. The method according to claim 2 wherein said sensor includes a heater element adapted to heat an area between said electrodes, wherein step (a) comprises the steps of:

(1) measuring $R_{elect}$ before activating the heater element and storing the value as $R_{OBD\_Rinit}$;

(2) activating the heater element for a first period of time; while periodically measuring $R_{elect}$, and storing the value as $R_{OBD\_Rhot}$;

(3) comparing $R_{OBD\_Rhot}$ to a predetermined percentage $K_{R\_ROBD\_Rcont\_Rpct1}$ of $R_{OBD\_Rinit}$;

(4) if $R_{OBD\_Rhot}$ is not less than the predetermined percentage $K_{R\_ROBD\_Rcont\_Rpct1}$ of $R_{OBD\_Rinit}$, then determining that $R_{elect}$ did not change in a manner consistent with heating a contaminated substrate; and (5) if $R_{OBD\_Rhot}$ is less than the predetermined percentage $K_{R\_ROBD\_Rcont\_Rpct1}$ of $R_{OBD\_Rinit}$ as determined in step (3) during said first period of time, then determining that $R_{elect}$ changed in a manner consistent with heating a contaminated substrate;

and step (c) comprises the steps of:

(1) maintaining activation of the heater element for a second period of time; while periodically measuring $R_{elect}$, and storing the value as $R_{OBD\_Rhot}$;

(2) comparing $R_{OBD\_Rhot}$ a predetermined percentage $K_{R\_ROBD\_Rcont\_Rpct2}$ of $R_{OBD\_Rinit}$;

(3) if $R_{OBD\_Rhot}$ is less than the predetermined percentage $K_{R\_ROBD\_Rcont\_Rpct2}$ of $R_{OBD\_Rinit}$, then determining that $R_{elect}$ did not change in a manner consistent with a contaminant being removed from the substrate; and (4) if $R_{OBD\_Rhot}$ is not less than the predetermined percentage $K_{R\_ROBD\_Rcont\_Rpct2}$ of $R_{OBD\_Rinit}$ as determined in step (3) during said first period of time, then determining that $R_{elect}$ changed in a manner consistent with a contaminant being removed from the substrate.

4. A diagnostic system for an electrically conductive particulate matter sensor comprising a substrate and two electrodes on said substrate adapted to collect particulate matter between the electrodes, thereby establishing an electrically conductive path through collected particulate matter between the electrodes that can be detected by measuring electrical resistance between the electrodes, $R_{elect}$, said system comprising a microprocessor in communication with the sensor and a storage medium including instructions for causing the microprocessor to implement a method comprising the steps of:

(a) commanding the provision of heat to the sensor in an amount sufficient to modify the electrical resistance of the substrate, and detecting whether $R_{elect}$ changes in a manner consistent with heating of a contaminant on the substrate;

(b) if $R_{elect}$ changes in a manner consistent with heating of a contaminant on the substrate in step (a), then diagnosing a contamination condition for the sensor;

wherein said sensor includes a heater element adapted to heat an area between said electrodes, and step (a) comprises the steps of:

(1) measuring $R_{elect}$ before activating the heater element and storing the value as $R_{OBD\_Rinit}$;

(2) activating the heater element for a first period of time; while periodically measuring $R_{elect}$, and storing the value as $R_{OBD\_Rhot}$;

(3) comparing $R_{OBD\_Rhot}$ to a predetermined percentage $K_{R\_ROBD\_Rcont\_Rpct}$ of $R_{OBD\_Rinit}$;

(4) if $R_{OBD\_Rhot}$ is not less than the predetermined percentage $K_{R\_ROBD\_Rcont\_Rpct}$ of $R_{OBD\_Rinit}$, then determining that $R_{elect}$ did not change in a manner consistent with heating a contaminated substrate; and (5) if $R_{OBD\_Rhot}$ is less than the predetermined percentage $K_{R\_ROBD\_Rcont\_Rpct}$ of $R_{OBD\_Rinit}$ as determined in step (3) during said first period of time, then determining that $R_{elect}$ changed in a manner consistent with heating a contaminated substrate.

5. A diagnostic system for an electrically conductive particulate matter sensor comprising a substrate and two electrodes on said substrate adapted to collect particulate matter between the electrodes, thereby establishing an electrically conductive path through collected particulate matter between the electrodes that can be detected by measuring electrical resistance between the electrodes, $R_{elect}$, said system comprising a microprocessor in communication with the sensor and a storage medium including instructions for causing the microprocessor to implement a method comprising the steps of:

(a) commanding the provision of heat to the sensor in an amount sufficient to modify the electrical resistance of the substrate, and detecting whether $R_{elect}$ changes in a manner consistent with heating of a contaminant on the substrate;

(b) if $R_{elect}$ changes in a manner consistent with heating of a contaminant on the substrate in step (a), then diagnosing a contamination condition for the sensor;

(c) if $R_{elect}$ changes in a manner consistent with heating of a contaminant on the substrate in step (a), then (i) maintaining the provision of heat for a predetermined time, (ii) determining after the lapse of the predetermined time whether $R_{elect}$ changes in a manner consistent with the contaminant being removed from the sensor, then (iii) if $R_{elect}$ changes in a manner consistent with the contaminant being removed from the sensor diagnosing that the contaminant was removed from the sensor , or if $R_{elect}$ does not change in a manner consistent with the contaminant being removed from the sensor diagnosing that the contaminant was not removed from the sensor.

6. The diagnostic system according to claim 5 wherein said sensor includes a heater element adapted to heat an area between said electrodes, wherein step (a) comprises the steps of:

(1) measuring $R_{elect}$ before activating the heater element and storing the value as $R_{OBD\_Rinit}$;

(2) activating the heater element for a first period of time; while periodically measuring $R_{elect}$, and storing the value as $R_{OBD\_Rhot}$;

(3) comparing $R_{OBD\_Rhot}$ to a predetermined percentage $K_{R\_ROBD\_Rcont\_Rpct1}$ of $R_{OBD\_Rinit}$;

(4) if $R_{OBD\_Rhot}$ is not less than the predetermined percentage $K_{R\_ROBD\_Rcont\_Rpct1}$ of $R_{OBD\_Rinit}$, then determining that $R_{elect}$ did not change in a manner consistent with heating a contaminated substrate; and (5) if $R_{OBD\_Rhot}$ is less than the predetermined percentage $K_{R\_ROBD\_Rcont\_Rpct1}$ of $R_{OBD\_Rinit}$ as determined in step (3) during said first period of time, then determining that $R_{elect}$ changed in a manner consistent with heating a contaminated substrate;

and step (c) comprises the steps of:

(1) maintaining activation of the heater element for a second period of time while periodically measuring $R_{elect}$, and storing the value as $R_{OBD\_Rhot}$;

(2) comparing $R_{OBD\_Rhot}$ a predetermined percentage $K_{R\_ROBD\_Rcont\_Rpct2}$ of $R_{OBD\_Rinit}$;

(3) if $R_{OBD\_Rhot}$ is less than the predetermined percentage $K_{R\_ROBD\_Rcont\_Rpct2}$ of $R_{OBD\_Rinit}$, then determining that $R_{elect}$ did not change in a manner consistent with a contaminant being removed from the substrate; and (4) if $R_{OBD\_Rhot}$ is not less than the predetermined percentage $K_{R\_ROBD\_Rcont\_Rpct2}$ of $R_{OBD\_Rinit}$ as determined in step (3) during said first period of time, then determining that $R_{elect}$ changed in a manner consistent with a contaminant being removed from the substrate.

* * * * *